(12) United States Patent
Kramer et al.

(10) Patent No.: US 9,797,849 B2
(45) Date of Patent: Oct. 24, 2017

(54) METHOD OF OPERATION AN IN SITU PROCESS PROBE

(71) Applicant: Rosemount Analytical, Inc., Solon, OH (US)

(72) Inventors: James D. Kramer, Homerville, OH (US); Joseph C. Nemer, Mayfield Heights, OH (US); Douglas E. Simmers, Massillon, OH (US)

(73) Assignee: Rosemount Analytical Inc., Solon, OH (US)

( * ) Notice: Subject to any disclaimer, the term of this patent is extended or adjusted under 35 U.S.C. 154(b) by 0 days.

(21) Appl. No.: 14/222,015

(22) Filed: Mar. 21, 2014

(65) Prior Publication Data

US 2014/0295570 A1 Oct. 2, 2014

Related U.S. Application Data

(60) Provisional application No. 61/806,626, filed on Mar. 29, 2013.

(51) Int. Cl.
*G01N 25/32* (2006.01)
*G01N 25/30* (2006.01)

(52) U.S. Cl.
CPC .... *G01N 25/32* (2013.01); *Y10T 436/208339* (2015.01)

(58) Field of Classification Search
CPC ........ G01N 25/32; G01N 25/30; G01N 25/28; G01N 25/22; G01N 25/20; G01N 25/00; Y10T 436/208339; Y10T 436/207497; Y10T 436/20; Y10T 436/00

USPC .... 436/130, 149, 137, 136, 127; 422/95, 94, 422/83, 50
See application file for complete search history.

(56) References Cited

U.S. PATENT DOCUMENTS

| 4,135,382 A | 1/1979 | Capone |
| 5,318,752 A | 6/1994 | Visser |
| 6,120,664 A | 9/2000 | Patel et al. |
| 8,635,899 B2 | 1/2014 | Bailey |

(Continued)

FOREIGN PATENT DOCUMENTS

| CN | 101329110 | 12/2008 |
| JP | 62-008107 | 1/1987 |

(Continued)

OTHER PUBLICATIONS

JPO Office Action and Translation for Patent Application No. 2012-520714, dated Jul. 30, 2013. 18 pages.

(Continued)

*Primary Examiner* — Christine T Mui
(74) *Attorney, Agent, or Firm* — Christopher R. Christenson; Kelly, Holt & Christenson, PLLC

(57) ABSTRACT

A process combustion transmitter is provided. The transmitter includes a process probe extendible into a flow of process combustion exhaust. The process probe has a measurement cell with an operating temperature that is above a flashpoint of process combustion fuel. The process probe includes a heater configured to heat the measurement cell to the operating temperature. Electronic circuitry is coupled to the measurement cell and to the heater. The electronic circuitry is configured to disengage power to the heater once process combustion heat is sufficient to maintain the measurement cell at the operating temperature and thereafter to maintain the heater in a de-energized state.

14 Claims, 4 Drawing Sheets

(56) References Cited

U.S. PATENT DOCUMENTS

| | | |
|---|---|---|
| 8,689,605 B2 | 4/2014 | Bailey |
| 2002/0182552 A1 | 12/2002 | Nielsen et al. |
| 2004/0182133 A1 | 9/2004 | Staphanos et al. |
| 2010/0073017 A1 | 3/2010 | Bevot et al. |
| 2011/0012040 A1 | 1/2011 | Bailey |
| 2013/0145814 A1 | 6/2013 | Bailey |

FOREIGN PATENT DOCUMENTS

| | | |
|---|---|---|
| JP | 05-226962 | 9/1993 |
| JP | 2004-366143 | 12/2003 |
| JP | 2007-084559 | 3/2007 |
| WO | 2011008743 A2 | 1/2011 |
| WO | 2011008743 A3 | 1/2011 |

OTHER PUBLICATIONS

First Official Action dated Jun. 18, 2013 in Chinese Patent Application Serial No. 201080012862.6, 14 pages.
International Search Report and the Written Opinion for International Patent Application No. PCT/US2010/041809 dated Jul. 31. 2012, 11 pages.
Shuk et al., "Zirconia Oxygen Sensor for the Process Application: State-of-the-Art", Sensor & Transducers Journal, vol. 90, Special Issue, Apr. 2008 by IFSA, www.sensorsportal.com, 12 pages.
"X-Stream O2 Combustion Flue Gas Transmitter", Rosemount Analytical Instruction Manual, Jan. 2009, www.raihome.com, 44 pages.
Search Report and Written Opinion from International application No. PCT/US2014/031561, date of mailing Aug. 20, 2014; date of filing Mar. 24, 2014. 11 pages.
Second Official Action dated Dec. 11, 2013 in Chinese Patent Application Serial No. 201080012862.6 with English Translation, 6 pages.
First Examination Report for Australian Patent No. 2014241683 dated Jan. 19, 2016, 3 pages.
First Official Action for Canadian Patent Application No. 2,903,401 dated Jul. 25, 2016, 4 pages.
Supplementary European Search Report for European Patent Application No. 14773891.8 dated Sep. 19, 2016, 9 pages.
First Office Action for Chinese Patent Application No. 201480004091.4 dated Apr. 19, 2016, 18 pages.
Second Chinese Office Action for Application No. 201480004091.4 dated Dec. 9, 2016, 16 pages with English Translation.
Office Action for the Canadian Patent Application No. 2,903,401, dated May 31, 2017, 3 pages.
Third Office Action for Chinese Patent Application No. 201480004091.4, dated Jun. 13, 2017, 16 pages with English translation.

METHOD OF OPERATION AN IN SITU PROCESS PROBE

CROSS-REFERENCE TO RELATED APPLICATION

The present application is based on and claims the benefit of U.S. Provisional Patent Application Ser. No. 61/806,626, filed Mar. 29, 2013, the content of which is hereby incorporated by reference in its entirety.

BACKGROUND

Industrial process industries primarily rely upon energy sources that include one or more combustion processes. Such combustion processes include operation of a furnace or boiler to generate energy from combustion, which is then used for the process. While combustion provides relatively low-cost energy, its use is typically regulated and combustion efficiency is sought to be maximized. Accordingly, one goal of the process management industry is to reduce the cost of fuel being burned, which also inherently minimizes production of greenhouse gases by maximizing combustion efficiency of existing furnaces and boilers.

In situ or in-process analyzers are commonly used for monitoring, optimizing, and/or controlling combustion processes. Typically, these analyzers employ sensors that are heated to relatively high temperatures and are operated directly above, or near, the furnace or boiler combustion zone. Known analyzers, such as those sold under the trade designation Oxymitter or Model 6888 O2 Combustion Flue Gas Transmitter available from Rosemount Analytical, Inc. of Solon, Ohio (an Emerson Process Management company), often employ zirconia oxide sensors heated to a temperature above approximately 736° Celsius (1300° Fahrenheit). If the combustion process should suffer a flame out condition, raw fuel and air are could be exposed to this sensor which, by virtue of its elevated temperature, could become an ignition source with the possibility of precipitating an explosion.

Some process analyzers are approved for hazardous area operation. Some approvals include those provided by the Canadian Standards Association (CSA), Factory Mutual (FM), ATEX, et cetera. Typically, hazardous area-approved analyzers include a flame arrestor that is added over the diffuser with the intent of quenching, or otherwise inhibiting, an explosion that might occur in front of the heated measurement cell, thereby preventing the ignition of the larger fuel volume in the boiler or combustion zone. These flame arrestors have been tested and approved in the past. However, it is believed that such arrestors can be improved. Moreover, the utilization of the flame arrestors may inhibit, to some degree, access to the measurement cell thereby increasing measurement lag. However, the utilization of flame arrestors adds expense and complexity to the system.

Some known process analyzers use flame scanners to detect a flameout and quickly and automatically cease fuel and/or air flow. Additionally, some efforts have been directed toward automatically creating a gaseous buffer between the measurement cell and the flue upon detection of a flameout. While these systems are effective, they add additional hardware and complexity thereby increasing system cost.

SUMMARY

A process combustion transmitter is provided. The transmitter includes a process probe extendible into a flow of process combustion exhaust. The process probe has a measurement cell with an operating temperature that is above a flashpoint of process combustion fuel. The process probe includes a heater configured to heat the measurement cell to the operating temperature. Electronic circuitry is coupled to the measurement cell and to the heater. The electronic circuitry is configured to disengage power to the heater once process combustion heat is sufficient to maintain the measurement cell at the operating temperature and thereafter to maintain the heater in a de-energized state.

DETAILED DESCRIPTION OF ILLUSTRATIVE EMBODIMENTS

Figure 1:
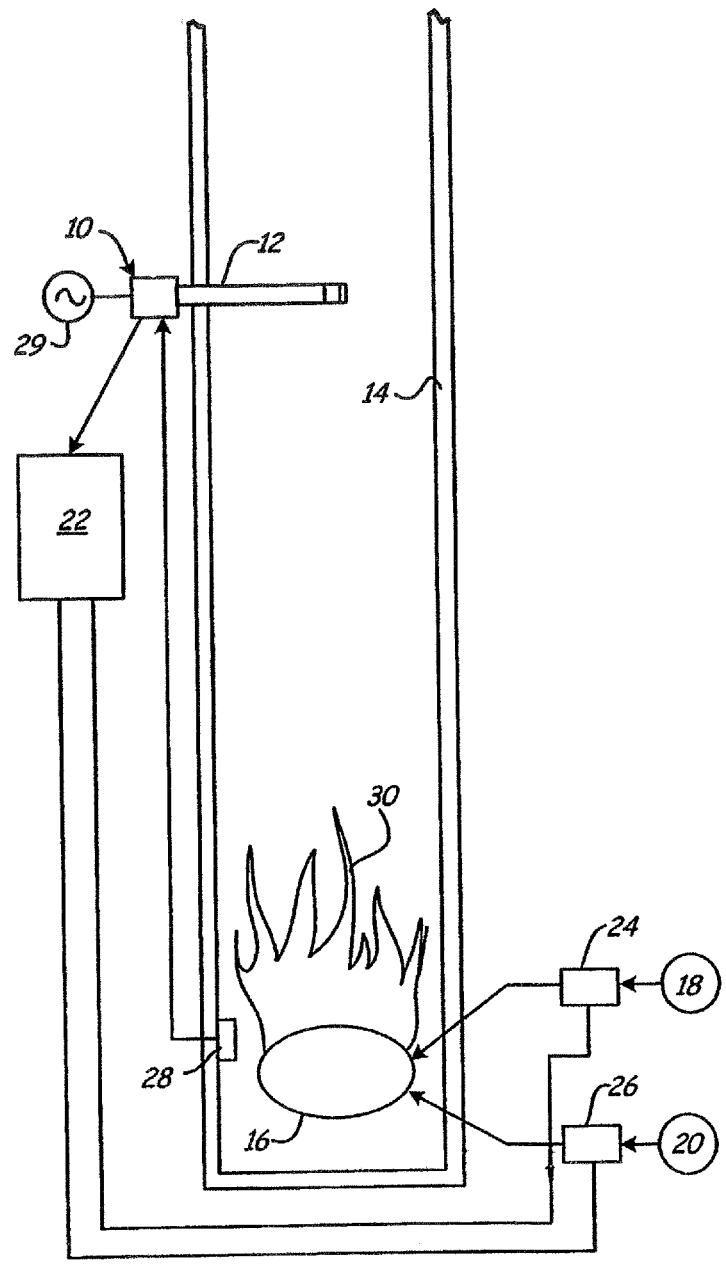
FIG. 1 is a diagrammatic view of an in situ combustion process analyzer with which embodiments of the present invention are particularly useful.

FIG. 1 is a diagrammatic view of an in situ process combustion analyzer with which embodiments of the present invention are particularly useful. Transmitter 10 can be any suitable analyzer including the 6888 O2 Combustion Flue Gas Transmitter listed above. Transmitter 10 includes a probe assembly 12 that is disposed within a stack or flue 14 and measures at least one parameter related to combustion occurring at burner 16. Typically, transmitter 10 is an oxygen transmitter, but can be any device that measures any suitable parameter related to the combustion process. Burner 16 is operably coupled to a source 18 of air or oxygen and a source 20 of combustible fuel. Each of sources 18 and 20 is preferably coupled to burner 16 through a valve of some sort to deliver a controlled amount of oxygen and/or fuel to burner 16 in order to control the combustion process. Transmitter 10 measures the amount of oxygen in the combustion exhaust flow and provides an indication of the oxygen level to combustion controller 22. Controller 22 controls one or both of valves 24, 26 to provide closed-loop combustion control. Transmitter 10 includes an oxygen sensor that typically employs a zirconia oxide sensor substrate to provide an electrical signal indicative of oxygen concentration, content or percentage in the exhaust. Zirconia oxide sensors operate at a temperature of about 700° Celsius and transmitter 10 includes, within probe assembly 12, an electrical heater that is operably coupled to AC power source 29. AC power source 29 can be a 110 or 220 VAC source that provides electrical energy to one or more electrical heating elements within probe assembly 12 to heat the zirconia oxide sensor substrate to a suitable temperature.

As can be appreciated, should burner 16 experience a flameout condition, it is possible that raw fuel and air could continue to flow from sources 20, 18, respectively, which materials could contact the hot zirconia oxide sensor, which could provide an unintended source of ignition. In order to address flameout conditions, prior art methods generally include a flame scanner 28 disposed to provide a signal indicative of the presence of flame 30 at burner 16. This flame scanner signal has been provided allow suitable reaction to the flameout condition. In the past, the flame scanner signal has been used to close a fuel valve and/or remove power from the analyzer thereby de-energizing the heater within probe assembly 12. In many cases, this removal of power allows rapid cooling of the zirconia oxide sensor to a temperature that is below the fuel ignition temperature, thereby creating a safe condition.

Figure 2:
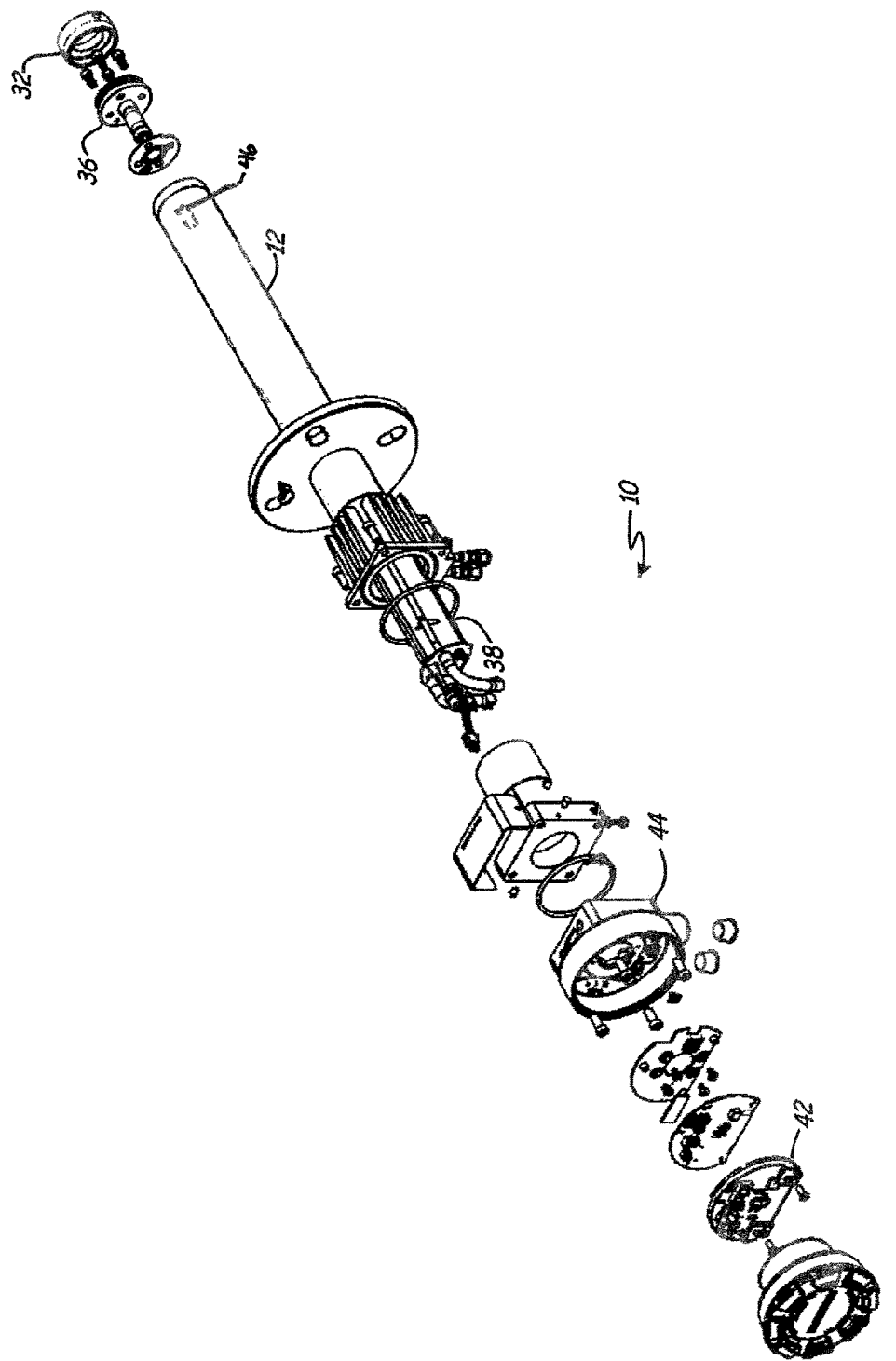
FIG. 2 is a diagrammatic exploded view of a process analytic oxygen transmitter in accordance with an embodiment of the present invention.

FIG. 2 is a diagrammatic view of an in situ process combustion analyzer in accordance with an embodiment of the present invention. Probe assembly 12 is generally configured to house the sensor core assembly which includes diffuser 32 disposed next to measurement cell 36. As described above, measurement cell 36 is operable at an elevated temperature and the elevated temperature is provided by electrical heater assembly 38, during startup. Measurement cell 36 and heater assembly 38 are electrically coupled to electronic circuitry of transmitter 10. The electronic circuitry is carried on electronics board 42 in housing 44. Additionally, temperature sensor 46 is also coupled to electronic circuitry on board 42. Temperature sensor 46 provides an indication of the temperature of the probe assembly 12 to the circuitry. Temperature sensor 46, in one embodiment, is separate from and in addition to the temperature sensor disposed within or proximate heater assembly 38 for thermal control of heater 38 during energization. In this way, temperature sensor 46 can provide an indication of process heat that is less affected by heat generated from heater assembly 38. In accordance with an embodiment of the present invention, the electronic circuitry is configured, through hardware, software or a combination thereof, to determine whether the temperature of probe assembly 12, as indicated by temperature sensor 46, has reached a heater shutoff threshold and upon reaching such threshold, latching, or otherwise placing, the heater power in an off condition until the electronic circuitry receives a reset signal. Thus, the process heat becomes the sole source of elevated temperature for measurement cell 36. If the process combustion should suffer a flameout condition, the loss of flame will quickly allow measurement cell 36 to cool such that it will not be a source of unintended ignition for non-combusted fuel. This passive protection feature can provide enhanced flameout protection in environments where a flame scanner is not technically and/or economically feasible. Additionally, while embodiments of the present invention are designed for use at flameout conditions, they are generally not employed during system startup. However, the system startup is generally a more controlled situation than a steady state flameout because a technician or operator is present during the system startup.

Figure 3:
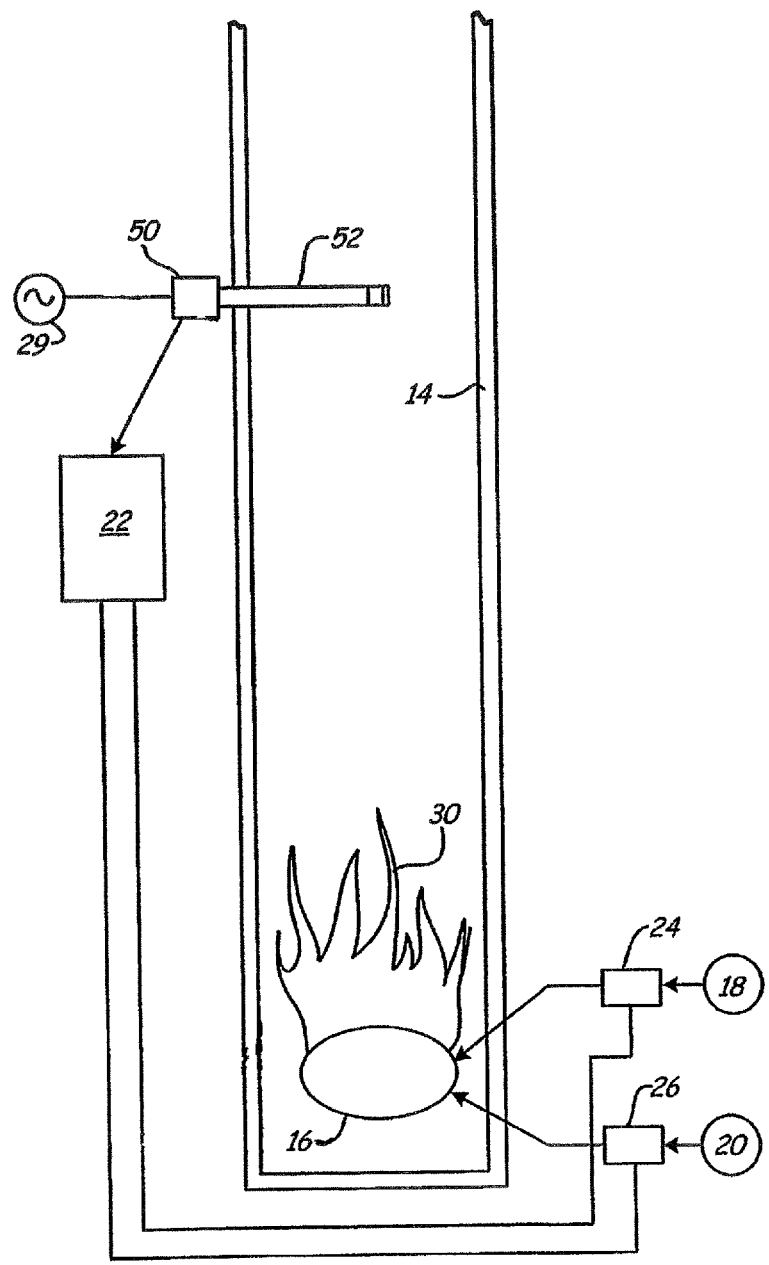
FIG. 3 is a diagrammatic view of an in situ combustion process analyzer in accordance with an embodiment of the present invention.

FIG. 3 is a diagrammatic view of an in situ combustion process analyzer in accordance with an embodiment of the present invention. Transmitter 50 includes probe assembly 52 containing therein a process gas sensor that operates at a temperature that is high enough to ignite unburned fuel from source 20 in the presence of air or oxygen from source 18 if flame 30 is lost. The combustion process analyzer shown in FIG. 3 does not require a flame scanner signal and thus the flame scanner is omitted from the combustion monitoring/control system. Transmitter 50, in accordance with an embodiment of the present invention, once reset, will allow its heater to operate until such time as it determines that process heat from flame 30 is sufficient to maintain a suitable elevated temperature of measurement cell 36, within probe assembly 52. Once the process heat is sufficient, heater 38 is disengaged and thereafter maintained in such condition until transmitter 50 is reset. Such reset can be in the form of a technician operating a reset button or control disposed on transmitter 50 or by sending a suitable reset command to transmitter 50 via a process communication loop or other suitable communication channel. This reset signal will generally be provided by the technician when the combustion process is starting up, and thus occurs under the technician's supervision. Since embodiments of the present invention provide protection against flameout conditions without the need for a flame scanner signal or a constant connection to a source of gas, such as calibration or purge gas, it is believed that embodiments of the present invention can be utilized in more applications than previous systems due to the simplicity and lower cost. Additionally, some embodiments of the present invention may be practicable without requiring the additional expense of a flame arrestor.

Figure 4:
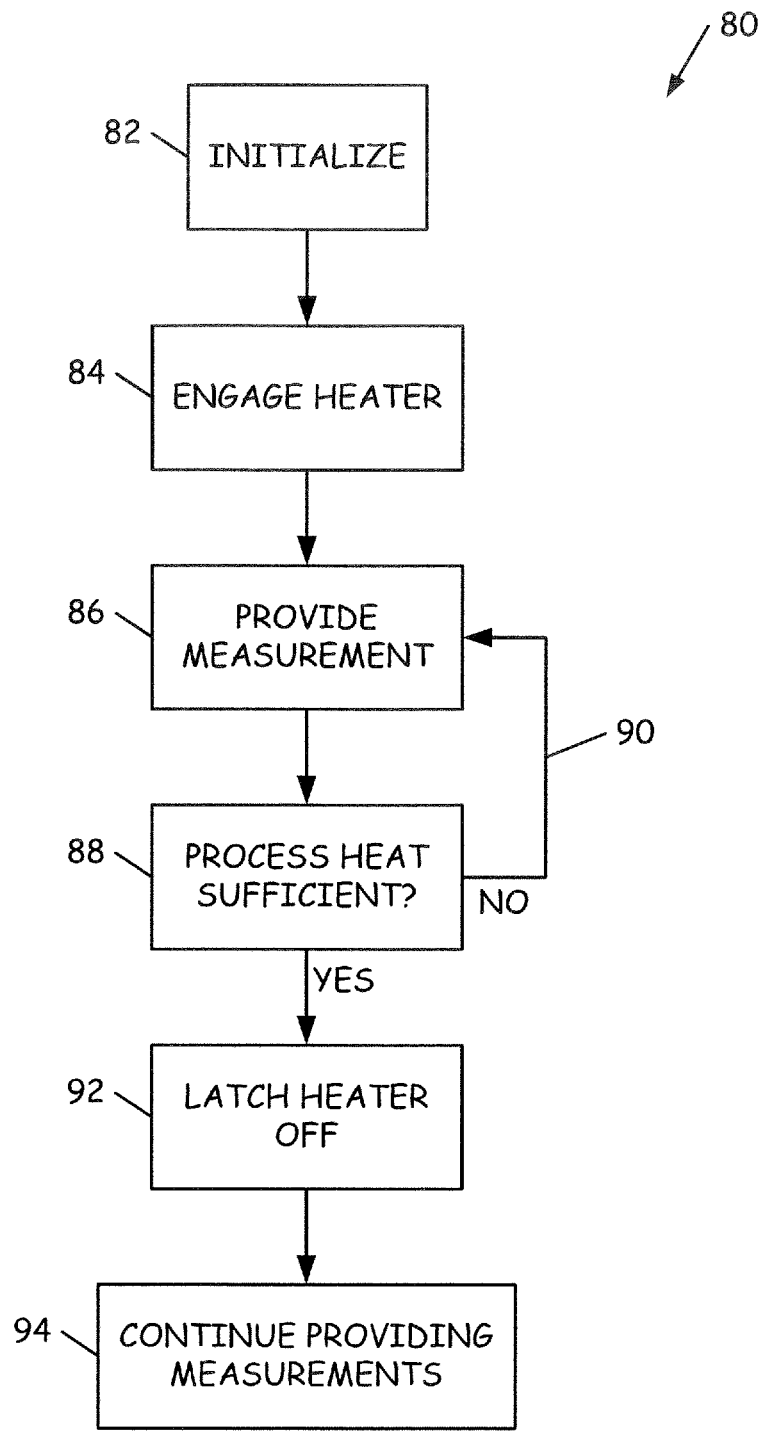
FIG. 4 is a flow diagram of a method of operating an in situ process analytic oxygen transmitter in accordance with an embodiment of the present invention.

FIG. 4 is a flow diagram of a method of operating an in situ process analytic oxygen transmitter in accordance with an embodiment of the present invention. Method 80 begins at block 82 where the in situ transmitter is initialized. Such initialization may include an initial power-up of the transmitter or, in the case of the transmitter already having power, the provision of a reset signal, either locally or via suitable communication techniques. Once initialized, the in situ transmitter will allow its heater to be engaged, as indicated at block 84. This allows the measurement cell to quickly reach its operating temperature such that useful process measurements can be provided. At block 86, the transmitter begins providing process variable information, such as oxygen content in combustion gases, to a process controller, such as controller 22, or other suitable device. At block 88, the transmitter determines if process heat is sufficient to maintain an elevated temperature of the measurement cell. If the process heat is not sufficient, control returns to block 86 via line 90, and the method loops until sufficient process heat is present. Once sufficient process heat is present, control passes to block 92, where the heater is latched in an off or de-energized state. The determination of whether sufficient process heat is present, in one embodiment, is performed automatically by transmitter 52. In such instance, transmitter 52 measures a temperature within or proximate probe 52 and compares the measured temperature with a threshold value. If the measured temperature is at or above the threshold value, for example, the heater can be de-energized and remain so until the transmitter receives a reset. However, embodiments of the present invention also include other techniques by which the heater may be latched off. For example, the transmitter may receive a "heater off" signal from the combustion controller, which has determined that the combustion heat is sufficient to maintain the measurement cell at a suitable elevated temperature for operation. Once the heater is latched off, control passes to block 94 where the process combustion transmitter continues providing process variable information regarding process combustion gases, such as oxygen content, while the heater is de-energized.

Although the present invention has been described with reference to preferred embodiments, workers skilled in the art will recognize that changes may be made in form and detail without departing from the spirit and scope of the invention.

What is claimed is:

1. A method of controlling a temperature of a process combustion transmitter, the method comprising:
   detecting an operating temperature of a process probe of the process combustion transmitter, the process probe being disposed within a flow of process combustion exhaust, the process probe having a measurement cell with an operating temperature that is above a flashpoint of process combustion fuel, wherein the process probe includes a heater configured to heat the measurement cell to the operating temperature;

comparing, using electronic circuitry coupled to the measurement cell, the indication of the detected operating temperature to a predetermined heater shutoff threshold;

de-energizing the heater power upon detecting that the heater shutoff threshold has been reached, such that combustion is a sole heat source for the measurement cell;

receiving a reset signal; and in response to the received reset signal, re-engaging the heater power.

2. The method of claim 1, wherein the measurement cell includes an oxygen sensor.

3. The method of claim 2, wherein the oxygen sensor is a heated sensor with an operating temperature at or above 700 degrees Celsius.

4. The method of claim 1, wherein the reset signal is generated locally at the process combustion transmitter.

5. The method of claim 1, wherein the electronic circuitry is configured to receive the reset signal via a process communication loop.

6. A method of operating an in situ process combustion transmitter having a measurement cell with an operating temperature above a flashpoint of combustion fuel, the method comprising:

initializing the transmitter, wherein initializing comprises instructing the transmitter to begin providing a process combustion variable output and to heat the measurement cell to the operating temperature;

receiving a temperature measurement, from the transmitter, of a process probe containing the measurement cell, wherein the temperature is measured using a temperature sensor separate from the measurement cell;

determining whether the measured temperature has reached a heater shutoff threshold by comparing the measured temperature to the heater shutoff threshold; and latching the heater in a de-energized state based on the determination that the measured temperature has reached the heater shutoff threshold such that only a process heat source provides heat to the measurement cell while the transmitter provides the process combustion variable output, and wherein latching the heater in the de-energized state comprises placing the heater in an off condition until a reset signal is received.

7. The method of claim 6, wherein determining whether the measured temperature has reached a heater shutoff threshold is performed by the process combustion transmitter.

8. The method of claim 6, wherein the operating temperature is about 700 degrees Celsius.

9. The method of claim 6, wherein the process combustion variable output is indicative of an oxygen content in combustion exhaust.

10. The method of claim 6, wherein initializing the process combustion transmitter includes providing a reset signal to the process combustion transmitter.

11. The method of claim 10, wherein the reset signal is provided locally to the process combustion transmitter.

12. The method of claim 10, wherein the reset signal is provided to the process combustion transmitter over a process communication channel.

13. The method of claim 1, wherein the reset signal comprises a command from a technician.

14. The method of claim 1, wherein the process combustion variable output is provided regardless of an energized state of the heater power.

* * * * *